United States Patent [19]

Crane

[11] Patent Number: 4,809,686
[45] Date of Patent: Mar. 7, 1989

[54] LATERAL SUPPORT FOR ANKLE

[76] Inventor: Larry A. Crane, 263 River Rd., Franklin, N.C. 28734

[21] Appl. No.: 99,559

[22] Filed: Sep. 22, 1987

[51] Int. Cl.⁴ .............................................. A61F 5/00
[52] U.S. Cl. ..................................... 128/80 H; 36/89; 128/166
[58] Field of Search ................. 128/80 H, 166; 36/88, 36/89, 90

[56] References Cited

U.S. PATENT DOCUMENTS 4,103,897 8/1978 Ostyn ........................... 128/80 H X

FOREIGN PATENT DOCUMENTS 526559 3/1930 Fed. Rep. of Germany ... 128/80 H

Primary Examiner—Edgar S. Burr
Assistant Examiner—Moshe I. Cohen
Attorney, Agent, or Firm—Shefte, Pinckney & Sawyer

[57] ABSTRACT

An ankle support prevents damage to a person's ankle by preventing severe lateral bending of the ankle. A support bar is pivotally attached to a high-top shoe, with the upper end of the bar well above the ankle and the lower end of the bar just below the foot. The upper end of the bar is fixed about centrally of the leg, while the lower end of the bar is fixed just forward of the heel. This results in having the bar pass along the front portion of the ankle. Both ends of the support bar can move somewhat at their connection points, so normal foot movement is not restricted while severe lateral motion is prevented.

7 Claims, 2 Drawing Sheets

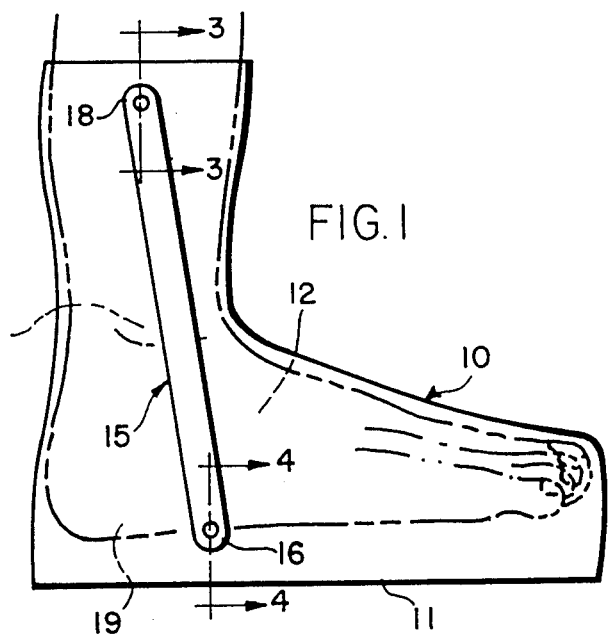
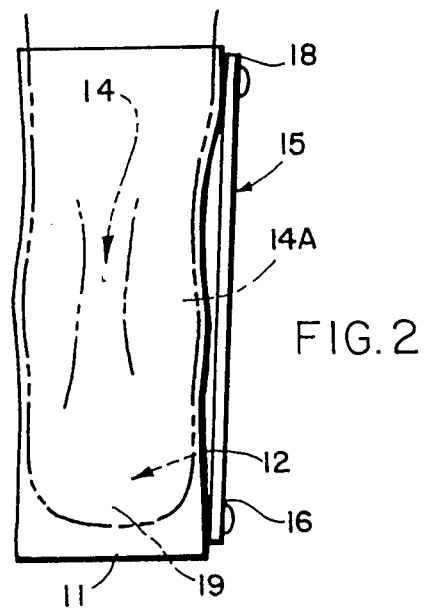

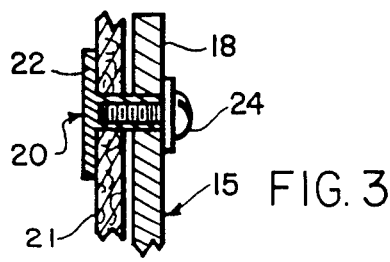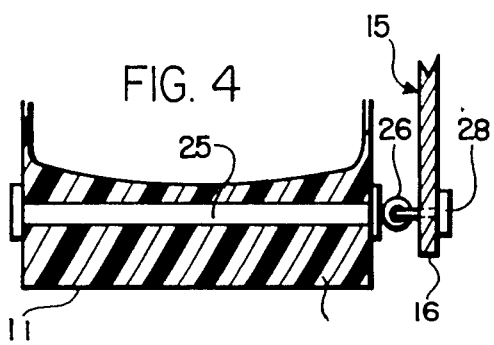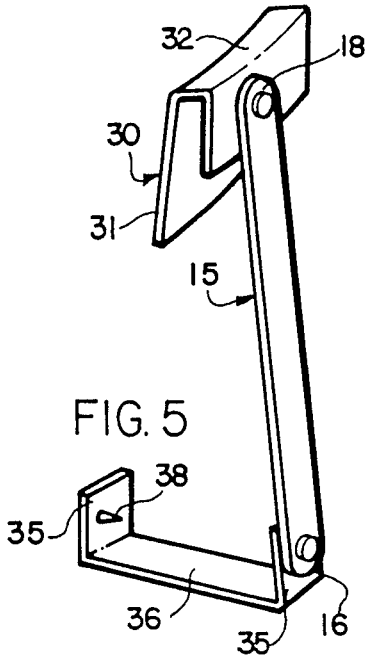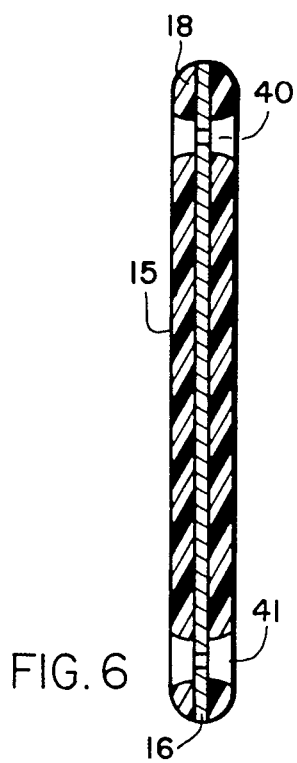

LATERAL SUPPORT FOR ANKLE

INFORMATION DISCLOSURE STATEMENT

In numerous undertakings, a person's ankle is subjected to lateral forces to a hazardous degree. The most common attempt to prevent damage by these lateral forces include the use of heavy shoes or boots to support the ankles, and the wrapping of the ankle with gauze or tape. All these efforts at supporting the ankle are insufficient when the ankle is subjected to strong lateral forces, or strong forces tending to fold the ankle in the lateral direction.

Another prior art effort at supporting the ankle against lateral motion is through the use of a generally rigid member attached above and below the ankle and spanning the ankle. These devices also have not been successful, the more common reasons for failure including improper length and placement of the rigid member. Additionally, the prior art ankle supports have not been appropriately attached to yield the needed support.

In view of the unsuccessful prior art efforts, there is still a need to provide an ankle support to protect the ankle against strong forces tending to bend the ankle laterally without unduly restricting motion of the foot.

SUMMARY OF THE INVENTION

This invention relates generally to ankle supports, and is more particularly concerned with a floating support member for preventing damage to the ankle from excessive bending in a lateral direction.

The present invention provides a rigid member anchored at a point above the ankle and at a point below the ankle and forwardly thereof. The rigid member extends above the ankle and below the ankle, spanning the ankle to provide mechanical support. Each end of the support member is fixed, preferably to a shoe or the like, in a resilient or floating manner.

The support of the present invention extends generally across the forward portion of the ankle, and is so located that, when the foot is moved upwardly, the support member remains sufficiently in the vicinity of the ankle to provide needed support, and when the foot is moved downwardly the support also remains sufficiently in the vicinity of the ankle to provide the needed support against lateral forces.

BRIEF DESCRIPTION OF THE DRAWINGS

These and other features and advantages of the present invention will become apparent from consideration of the following specification when taken in conjunction with the accompanying drawings in which:

FIG. 1 is a side elevational view showing a shoe with an ankle support made in accordance with the present invention carried on the shoe, and a foot shown in phantom;

FIG. 2 is a rear elevational view of the shoe illustrated in FIG. 1;

FIG. 3 is an enlarged cross-sectional view taken substantially along the line 3—3 in FIG. 1;

FIG. 4 is an enlarged cross-sectional view taken substantially along the line 4—4 in FIG. 1;

FIG. 5 is a perspective view showing a support member made in accordance with the present invention, and including means for selectively attaching the support member to a shoe; and, FIG. 6 is a longitudinal cross-sectional view through a support member showing optional padding for the support member.

DETAILED DESCRIPTION OF THE EMBODIMENTS

Referring now more particularly to the drawings, and to those embodiments of the invention here presented by way of illustration, FIG. 1 is a somewhat schematic view, illustrating generally a high-top shoe designated at 10 having a sole 11. A foot is shown in broken lines since the ankle support of the present invention is to be placed appropriately relative to the foot for maximum protection. Thus, it will be seen that the foot is designated generally at 12, while the ankle is shown at 14.

It will be understood by those skilled in the art that the ankle is not a single point or a single bone. Thus, for the present discussion some definitions need to be provided. The ankle as a whole is a joint that allows the foot to move with respect to the leg. The protuberances that are popularly called the ankle are parts of the tibia and fibula, the tibia providing the inside protuberance and the fibula providing the outside protuberance. These protuberances will be referred to as the inside ankle (tibia) and the outside ankle (fibula), and the general term ankle will apply to the joint as a whole.

The support member is indicated at 15 and is shown as comprising a strip of material, such as steel or the like. While the specific material is not important, one must select a material having sufficient strength to withstand the forces to be encountered. The support member 15 is fixed to the shoe 10 approximately in the vicinity of the shoe sole 11, and below the foot 12. The upper end 18 of the support 15 is fixed to the side of the shoe 10 at a point definitely above the ankle 14. As will be seen in FIG. 1, the upper end 18 of the support 15 is substantially centrally of the profile of the leg, or shoe 10, while the lower end 16 of the support member 15 is somewhat forwardly of the leg. The lower end 16 of the support member 15 will generally be located just forward of the heel 19 of the foot 12, approximately on the line between the tarsals and the metatarsals.

It will be realized that, as the foot 12 is moved to pivot at the ankle 14, the lower end 16 of the support member 15 will move, rotating about the end 18. To some extent, the mechanical arrangement is such as to allow such motion without interference. Nevertheless, realizing that the motion of the foot will not constitute a precise pivotal motion at the ankle, and that the ankle does not constitute a truly precise mechanical pivot, it will be realized that the support member 15 must allow some movement of the shoe 10 with respect to the support member 15. Such motion is contemplated in the present invention.

Looking now at FIG. 2 of the drawings, the shoe 10 is again shown in full lines with the foot 1 shown in phantom. In FIG. 2 it will be seen that the lower end 16 of the support 15 is below the heel 19, and the upper end 18 of the support 15 is above the ankle 14. The length of the support member 15 must be sufficient to extend above and below the ankle to give an adequate mechanical advantage in supporting the ankle.

Continuing to look at FIG. 2 of the drawings, it should be understood that, if there is a force tending to cause the foot 12 to bend at the ankle 14, the ankle 14 will bear against the support member 15 trying either to bend the member 15 or to remove the end 16 and/or 18 from the connection to the shoe. With this in mind, it should be understood that, if the lower end 16 is firmly attached to the shoe and the outside ankle 14A is urged against the support member 15, the end 16 acts as a fulcrum while the outside ankle 14A acts as the force, then the upper end 18 plays the part of the resistance. With this analysis, it will be understood that if the distance between the ankle 14 and the upper end 18 is very short, the force of the outside ankle 14A against the support member 15 will have a mechanical advantage in moving the upper end 18. The motion of the upper end 18 may be in the form of tearing the end from its connection, and may result simply in sufficient distortion of the shoe that the foot 12 can move within the shoe. Regardless of the particular form of the failure, the ankle 14 is subject to damage.

With the foregoing in mind, it will be clear that the upper end 18 of the support 15 may be as far up the leg as one desires, though the connection should be below the knee for obvious mechanical reasons. The preferred embodiment, however, will place the upper end 18 of the support 15 generally at the top of fairly conventional high top shoes or boots.

Looking now at FIG. 3 of the drawings, it will be seen that one form of connection of the support member 15 to the shoe is to provide a threaded fitting 20 extending through the material 21 of the shoe 10. Though not here shown, it is contemplated that reinforcement in the form of molded plastic members, stitching or the like will be used around the hole 22 through which the fitting 20 passes. A screw 24 then extends through the upper end 18 of the support member 15 to be received by the threaded fitting 20.

With this arrangement, it will be understood that the material 21 is flexible, and may be leather, canvas or the like. The fact that the material 21 is flexible will allow the fitting 20 to vary somewhat, hence allow the upper end 18 of the support 15 to move, or float.

Looking at FIG. 4 of the drawings, a slightly different arrangement is shown for connection of the support member 15 to the shoe 10. In FIG. 4 there is a pin 25 passing through the sole 11 of the shoe 10, the pin 25 terminating in a loop 26. The support member 15 is then provided with a mating loop member 28. With the two loops, or eyes, engaging each other it will be understood that there is sufficient play in the joint to allow the desired floating of the support member 15.

Those skilled in the art will devise numerous connections for fixing the support member 15 to shoes or the like, and the two above described connections are by way of illustration only.

Attention is now directed to FIG. 5 of the drawings which discloses a connection means that will allow a user to fix the support member to a selected pair of shoes. The support member is again designated at 15, with an upper end 18 and a lower end 16. The upper end 18 of support member 15 is pivotally connected to a clip designated at 30, the clip 30 being somewhat curved as viewed from the top, and having an inner flange 31 that is adapted to be received within a boot. The upper curved portion 32 then spans the upper edge of the boot while the outer flange 34 lies along the outside of the boot and provides for connection of the support member 15.

The lower end 16 of the support member 15 is pivoted to an upwardly turned flange 35, the flange 35 being one of a pair of such flanges connected by a transverse member 36. It will be seen that the flanges 35 include inwardly projecting members such as the member 38 to engage a shoe.

From the above discussion, it should be understood that the transverse member 36 will be placed beneath the shoe, adjacent to the heel of the shoe. The flanges 35 will then extend upwardly at each side of the shoe and the inward projections 38 will engage the sole of the shoe sufficiently to prevent dislocation of the members. The clip 30 will engage the upper portion of the shoe or boot, and it will be seen that the inner flange 31 is long enough that the clip will not be easily removed from the boot.

With this in mind, it will be seen that lateral forces against the support member 15 will be restrained by the inner flange 31 of the clip 30, and by the flanges 35 of the lower member.

When the support member of the present invention is utilized in some environments, the support member may take the form of a simple metal member as is shown in FIGS. 1-5 of the drawings. In some situations, such as in sporting events and the like, it may be desirable to provide some form of padding for the support member, either on the outside to protect other participants, or on the inside to protect the wearer. Such an arrangement is shown in FIG. 6 of the drawings where it will be seen that expanded plastic material is shown covering both sides of the support member 15. Appropriate openings 40 and 41 are provided in the vicinity of the holes in the upper end 18 and lower end 16. Those skilled in the art will therefore understand that foamed plastic such as polyurethane or the polyolefins may be utilized, sheets of material or fibrous padding may be utilized, and of course rubber, either foamed or not may be used. Further, various forms of covering may be provided for the support member 15, both for utilitarian and for aesthetic purposes.

While some of the prior art ankle supports have rendered the supports very wide in the vicinity of the ankle, it should be noted that the additional width appears to serve no utilitarian function. It is the strength substantially along the line between the upper and lower connections that is important, and this fact renders it important to place the support member 15 substantially as shown in FIG. 1 of the drawings. As was discussed briefly, the support member 15 should be placed somewhat at the forward portion of the ankle 14 so that, as the foot is moved up the support member 15 will remain in the vicinity of the ankle 14, and as the foot is moved down the support member 15 will still remain in the vicinity of the ankle 14 to provide the needed support.

In FIG. 1, the support 15 is placed on the outside of the shoe 10 so the support 15 extends along the forward position of the ouside ankle 14A. If the support 15 is placed on the inside of the shoe, the support will be located to extend along the forward portion of the inside ankle 14B. It is also contemplated that supports 15 may be placed both inside and outside, though it appears that the use of only one support 15 is highly satisfactory.

It will of course be understood that the support member 15 may be made wider, or in the form of struts or the like, or in various other forms for aesthetic purposes. Further, trademarks and the like may be painted on the support, or worked into the struts making up the support as desired.

It will therefore be understood by those skilled in the art that the particular embodiments of the invention here presented are by way of illustration only, and are meant to be in no way restrictive; therefore, numerous changes and modifications may be made, and the full use of equivalents resorted to, without departing from the spirit or scope of the invention as outlined in the appended claims.

I claim:

1. An ankle support, for preventing damage to a person's ankle through lateral bending of the ankle, said ankle support comprising a generally rigid elongate support member having an upper end and a lower end, said support member extending adjacent to an ankle to be supported, first anchoring means for fixing said upper end of said support member at a first predetermined point above said ankle to be supported, said upper end of said rigid member being connected to said first anchoring means for rotation about said first anchoring means, second anchoring means for fixing said lower end of said support member at a second predetermined location below said ankle to be supported, said lower end of said rigid member being connected to said second anchoring means for rotation about said second anchoring means, said first predetermined location above said ankle to be supported and said second predetermined location below said ankle to be supported being positioned such that said support member extends between said first and second anchoring means in an essentially straight line along the forward portion of said ankle to be supported, the arrangement being such that said rotation of said rigid member about said first and second anchoring means permits generally unrestricted normal axial movements of the foot while constantly positioning said rigid member at a location adjacent said ankle to prevent lateral bending thereof.

2. An ankle support as claimed in claim 1, wherein said ankle support is in combination with a shoe, said first anchoring means including a fitting extending through the upper portion of said shoe, said fitting receiving said support member thereon.

3. An ankle support as claimed in claim 1, wherein said ankle support is in combination with a shoe, said first anchoring means including a clip receivable over the upper edge of said shoe, said clip including an outer flange for pivotally receiving said upper end of said support member.

4. An ankle support as claimed in claim 1, wherein said ankle support is in combination with a shoe, said second anchoring means including a pin passing through the sole of said shoe, one end of said pin pivotally receiving said lower end of said support member.

5. An ankle support as claimed in claim 1, wherein said ankle support is in combination with a shoe, said second anchoring member including a pair of flanges engaging said shoe, at least one of said flanges pivotally receiving said lower end of said support member.

6. An ankle support as claimed in claim 1, said support member comprising a generally flat elongate member, and further including padding means carried by at least one side of said flat elongate member.

7. An ankle support as claimed in claim 1, with at least one of said first or second anchoring means being secured to a flexible material that permits limited floating movement of said anchoring means and the end of said rigid member attached thereto.

* * * * *